United States Patent [19]

Miller et al.

[11] Patent Number: 4,587,044
[45] Date of Patent: May 6, 1986

[54] LINKAGE OF PROTEINS TO NUCLEIC ACIDS

[75] Inventors: Paul S. Miller, Baltimore; Paul O. P. Ts'O, Lutherville, both of Md.

[73] Assignee: The Johns Hopkins University, Baltimore, Md.

[21] Appl. No.: 528,573

[22] Filed: Sep. 1, 1983

[51] Int. Cl.$^4$ ............... C07K 17/00; C07H 17/00; C07H 15/12
[52] U.S. Cl. .................. 530/211; 536/22; 536/28; 536/29; 435/6; 435/177; 435/180; 435/181; 424/85; 530/358
[58] Field of Search ............. 260/112 R, 112.5 R, 260/112 B; 536/22, 28, 29; 424/85; 435/6, 177, 180, 181

[56] References Cited

U.S. PATENT DOCUMENTS

| | | | |
|---|---|---|---|
| 3,687,808 | 8/1969 | Merigan et al. | 424/85 |
| 4,219,645 | 8/1980 | Stark et al. | 536/29 |
| 4,259,232 | 3/1981 | Carrico et al. | |
| 4,358,535 | 11/1982 | Falkow et al. | 435/6 |
| 4,426,517 | 1/1984 | Hsiung | 536/28 |
| 4,446,315 | 5/1984 | Marquez | 536/84 |
| 4,471,113 | 9/1984 | MacCoss | 536/29 |
| 4,478,914 | 10/1984 | Giese | 428/407 |

OTHER PUBLICATIONS

Chem. Abst. #98, 1573991, Merlino et al., Versatile Method for Coupling of Protein to DNA.
Chem. Abst. #81, 117061, Aharonov et al., Immunogenicity and Antigenic Specificity of a Glutaraldehyde Crosslinked . . . Protein Conj.
Chem. Abst. #78, 156268q, E coli Initiation Factor, Groner et al.
Nucleic Acids Res. 9(10), 1981, Westermann et al., Cross-Linking of Mettrna . . . Small Ribosomal Subunits.
Kennedy et al., "Protein-Protein Coupling Reactions and the Applications of Protein Conjugation", Clinica Chemica Acta 70, 1976, pp. 1–31.
Ghase et al., "Preparation of Antibody-Linked Cytotoxic Agents", Methods of Enzymology, vol. 93, 1983, pp. 280–332.
Langer et al., "Enzymatic Synthesis of Biotin-Labeled Polynucleotide: Novel Nuclear Acid Affinity Probes" PNAS vol. 78(11), 1981, pp. 6633–6637.
Leary et al., "Rapid and Sensitive Colorimetric Method for Visualizating Brotin-Labeled DNA . . . Bio Blots" PNAS vol. 80, 1983, pp. 4045–4049.

Primary Examiner—John Kight
Assistant Examiner—Garnette D. Draper
Attorney, Agent, or Firm—Cushman, Darby & Cushman

[57] ABSTRACT

A nucleic acid-protein conjugate which is specific with respect to a selected living cell is prepared by linking said nucleic acid to a protein specific to said living cell.

47 Claims, 3 Drawing Figures

ELUTION PROFILES OF SEPHACRYL S-200 COLUMNS FOR REACTIONS 2+3 FROM TABLE 4

ANTIVIRAL STATE INDUCTION ACTIVITY OF $rI_n \cdot rC_n$-LINKED CON A

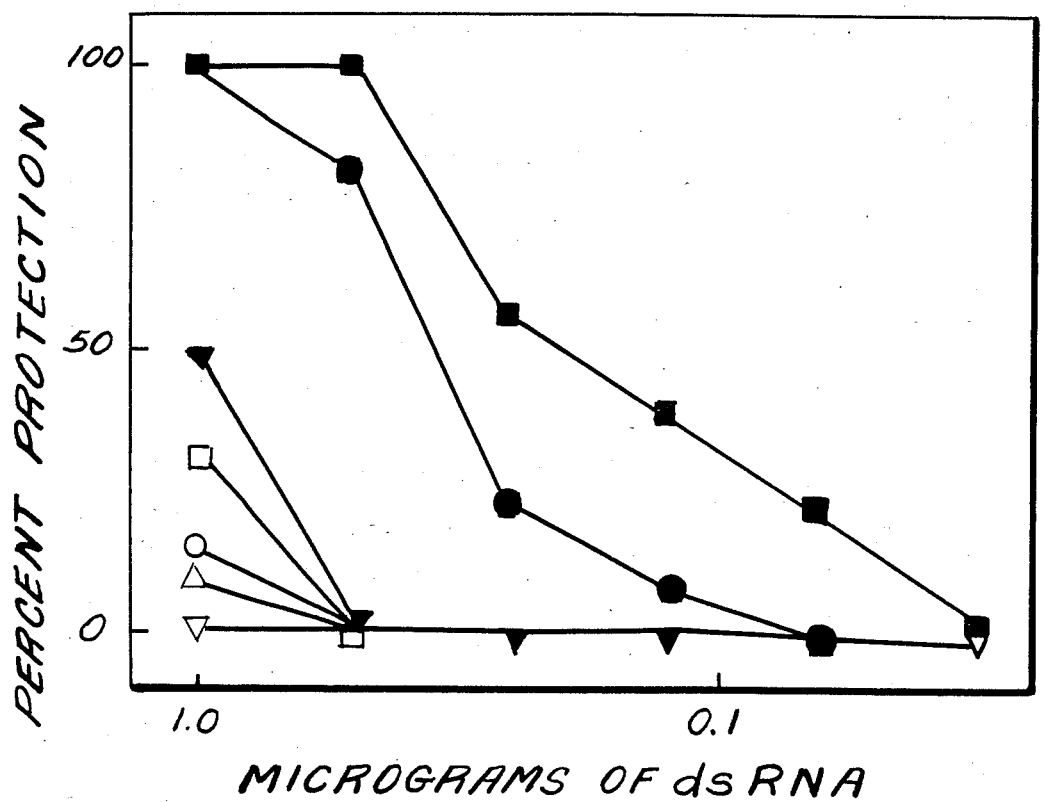

4,587,044

LINKAGE OF PROTEINS TO NUCLEIC ACIDS

BACKGROUND OF THE INVENTION

It is well known that nucleic acids, including, for instance, double stranded ribose nucleic acid, have been employed as interferon inducers, cytotoxic agents or for the purpose of gene-transfer. However, one attendant disadvantage is that such nucleic acids exhibit little if any cell-type specificity. It has now been found that this disadvantage can be overcome by linking or attaching the nucleic acid to a protein whereby the cell-type target is chosen by the protein molecule. After binding to the cell surface, the nucleic acid can then interact with its cell-surface receptor, or if the protein is internalized by receptor-mediated endocytosis, the nucleic acid can interact with one of the intracellular nucleic acid-dependent enzymes and assert its action. In addition, through protein-nucleic acid linkage, the uptake of nucleic acid can be accompanied by an enzyme to increase the biological effectiveness of the nucelic acid-enzyme conjugate.

GENERAL DESCRIPTION OF THE INVENTION

The present invention thus relates to proteins linked to nucleic acids which proteins provide vehicles to enhance the uptake or specific interaction of the nucleic acid with living cells and to a method for preparing the same.

The protein selected for linkage to the nucleic acid is one which interacts with receptors or antigenic sites on the surface of the target cell, thereby bringing the nucleic acid into close proximity of the receptor sites on the target cell or permitting the nucleic acid to be taken into the target cell via the process of pinocytosis/endocytosis.

The method of preparing a nucleic acid-protein conjugate wherein the said conjugate is specific with respect to a selected living cell comprises linking said nucleic to the desired protein which is specific to said living cell.

More particularly, the process of the present invention to produce a nucleic acid-protein conjugate, said conjugate being specific with respect to a selected living cell comprises modifying said nucleic acid so as to contain a group reactive with a bifunctional crosslinking agent and reacting said crosslinking agent with said modified nucleic acid and with a protein specific to said living cell.

Several methods have been developed to modify the nucleic acid so that it can be linked to a protein.

One such method involves esterifying the 2'—OH group of the nucleic acid with a saturated or unsaturated aliphatic dicarboxylic acid or anhydride. The terminal free carboxyl group is then reacted with a diaminoalkane, generally in the presence of an activator to provide the aminoalkyl derivative. The terminal primary amino group of this derivative serves as a site for further reactions with bifunctional crosslinking reagents. Generally the esterification and amidation reactions are carried out in an aqueous medium and preferably the aqueous medium for the esterification reaction is an aqueous pyridine/acetonitrile solution.

As a variant of this method the terminal free carboxyl group of the ester derivative is reacted with cysteamine to provide a terminal —SH group on this modified nucleic acid or with 2,2'-dithiobis(amino ethane) to provide a terminal—S—SR group, these terminal groups also serving as sites for further reactions with bifunctional crosslinking agents.

Conveniently the dicarboxylic acid employed can be succinic acid or its anhydride although other dicarboxylic acids such as malonic, glutaric, adipic, pimelic and sebacic or the anhydrides thereof can be employed.

The diaminoalkane, having the formula $H_2N-(CH_2)_n-NH_2$, wherein n is, for instance, 2-12, is preferably ethylenediamine.

The extent of the nucleic acid modification can be controlled by varying the reaction conditions. Generally this modification reaction is carried out at ambient temperature although elevated or reduced temperatures can also be employed.

In another variant of the method to modify the nucleic acid, the nucleic acid can be subjected to a bisulfite-catalyzed transamination reaction. In this modification procedure the C-4 amino group of cytosine is replaced by a diaminoalkane, which can be the same as that defined above. The nucleic acid, either single-stranded or double-stranded RNA or DNA is treated with a diaminoalkane, such as ethylenediamine, in the presence of sodium bisulfite. The bisulfite forms an adduct with cytosine by adding across the 5,6 double bond of the base. The diaminoalkane then displaces the 4-amino group by nucleophilic attack at C-4. The 5,6 double bond is reformed when the bisulfite is removed from the solution. The resulting aminoalkyl group which is now attached to the nucleic acid serves as a reaction site for crosslinking agents.

In still another variant of this method the nucleic acid can be enzymatically modified. In one variation of this embodiment aminoethyldeoxycytidine 5'-triphosphate is used as a substrate for DNA polymerase I so as to incorporate aminoethyldeoxycytidine residues into double-stranded DNA via a nick translation reaction. The aminoethyldeoxycytidine 5'-triphosphate can be prepared by sodium bisulfite catalyzed transamination of deoxycytidine 5'-triphosphate. The level of incorporation can be controlled by varying the ratio of aminoethyldeoxycytidine 5'-triphosphate to deoxycytidine 5'-triphosphate employed in the reaction.

In a second variation, the aminoethyldeoxycytidine 5'-triphosphate is employed as a substrate for deoxynucleotidyl terminal transferase. In this situation aminoethyldeoxycytidine residues are incorporated as a single-stranded tail at the 3'-end of the DNA chain. This procedure can be used for both double-stranded and single-stranded deoxypolynucleotides.

In a third variation, the aminoethylcytidine 5'-diphosphate or aminoethylcytidine 5-triphosphate are used as substrates for polynucleotide phosphorylase or RNA polymerase, respectively. The aminoethylcytidine residues are added to the 3'-end of single-stranded ribopolynucleotides. The level of incorporation and the length of the modified tail can be controlled by adjusting the substrate concentration and the reaction conditions.

Several methods have been developed for linking the modified nucleic acid to a desired protein or a group of proteins. As indicated above the modified nucleic acid contains a terminal aminoalkyl or thioethyl group which is employed as a reactive site for crosslinking with the protein. Various crosslinking agents can be employed.

In one embodiment, the nucleic acid aminoethyl group is reacted with a homobifunctional acylating agent, such as dithiobis(N-hydroxylsuccinimidylpropionate). This crosslinking agent has a N-hydroxysuccinimide group at both ends of the molecule, one of which reacts with the 2-amino group of the nucleic acid aminoethyl arm. The N-hydroxysuccinimide group at the other end of this homobifunctional acylating agent reacts with amino groups of the protein.

In another embodiment, the nucleic acid aminoethyl group is acylated with a heterobifunctional crosslinking agent such as N-succinimidyl 2-pyridyldithiopropionate and the disulfide linkage is reduced to generate a free —SH group. The amino groups of the protein are acylated with, for instance, N-succinimidyl 2-pyridyldithiopropionate. The resulting acylated nucleic acid and protein are then conjugated by a disulfide exchange reaction.

In still another embodiment, the amino groups of the protein are acylated with a heterobifunctional crosslinking agent such as N-succinimidyl 4'-(p-maleimidophenyl) butyrate. This crosslinking agent has a N-hydroxysuccinimide group at one end of the molecule which reacts with the modified nucleic acid amino group. The maleimide moiety at the other end of the heterobifunctional agent reacts with the free —SH groups of the protein.

In yet another embodiment, the amino groups of the protein are acylated with a heterobifunctional agent such as N-succinimidyl 4'-(p-maleimidophenyl) butyrate. The thio group of the thioethyl-modified nucleic acid then reacts with the maleimide moiety of the acylated protein.

In yet a further embodiment the nucleic acid ethylamino group and the amino groups of the protein are each acylated with biotinyl N-hydroxysuccinimide. The biotin moieties introduced into both the protein and nucleic acid have an extremely high affinity ($K\ dis = 1 \times 10^{-5}$ M) for the glycoprotein avidin and vitamin H avidin. Each molecule of avidin has four binding sites for biotin. Thus, the acylated nucleic acid and acylated protein are linked by an avidin bridge.

In another embodiment, the biotinated nucleic acid and protein, prepared as described immediately above, can be linked via a monoclonal antibody which specifically recognizes biotin. The antibody thus takes the place of avidin as noted above.

Alternatively, the nucleic acid can be linked directly with an antibody, species 1. This antibody from species 1 is selected to cross-react with IgG or IgM antibodies of another species, species 2. For example, the nucleic acid can be linked to goat antimouse IgG. Species 2 antibodies, mouse antibodies, are then prepared which specifically interact with selected carrier proteins or surface antigens of target cells, including human cells. The nucleic acid can then be physically linked to a variety of carrier proteins and can be guided to the target cell via interaction between its antibody, species 1 and a variety of species 2 antibodies, each of which can interact with a specific carrier protein/surface antigen of the target cell.

DETAILED DESCRIPTION OF THE INVENTION

I—Modification of Nucleic Acids

Figure 1:
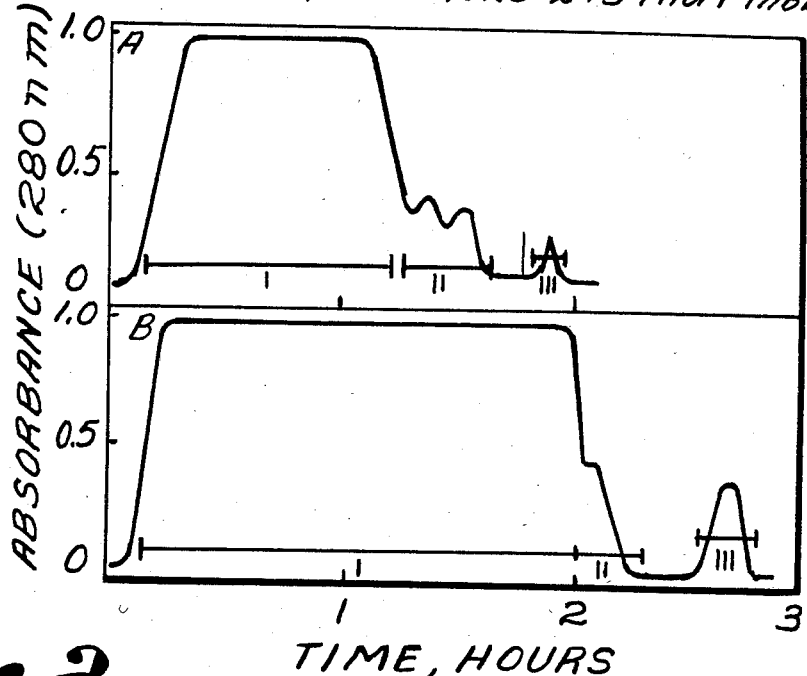

A. Esterification of nucleic acid followed by amidation of the terminal free carboxyl group of said ester.

As noted above, several methods have been developed, in accordance with the present invention, to modify the nucleic acid for subsequent linkage to a desired protein.

One such method involves the esterification of the 2'—OH groups of the nucleic acid with a saturated or unsaturated aliphatic dicarboxylic acid with the terminal free carboxyl group of the resulting ester being amidated with a diaminoalkane, cysteamine or 2,2'-dithiobis(aminoethane).

Representative of this nucleic acid modification reaction is the following:

(3'-5') cyclic inosine monophosphate is prepared from p<A by deamination in 50% acetic acid and sodium nitrite. Complete conversion of p<A to (3'-5') cyclic inosine monophosphate was verified by paper electrophoresis (0.05M triethylammonium carbonate, pH 7.5) with appropriate authentic markers. The pure (3'-5') cyclic inosine monophosphate was separated out of the reaction mixture by conventional charcoal chromatographic procedures.

The initial reaction between succinic anhydride and (3'-5') cyclic inosine monophosphate, at a mole ratio of 10:1 was carried out. The extent of reaction was determined by paper electrophoresis (0.05M triethylammonium carbonate, pH 7.5) or reversed phase high pressure liquid chromatography (ODS-III, 0.2M $NH_4CO_3$, pH 7.6, 0.1% $CH_3CN$).

Because of the presence of a cyclic phosphate group, the only reactive site accessible in (3'-5') cyclic inosine monophosphate is the 2'-hydroxyl group. Ester bond formation with succinic anhydride and a free hydroxyl group is relatively efficient provided the reaction is run under appropriate conditions. As can be seen in Table 1, below, a series of solvent systems were examined to determine the relative effects of $H_2O$ and other solvents on succinylation.

TABLE 1

| | Succinylation of (3'-5') cyclic inosine monophosphate | |
|---|---|---|
| Reaction Number | Solvent $H_2O$:DMF:Pyridine:$CH_3CH$ | Percent succinylate (3'-5') cyclic inosine monophosphate |
| 1 | 0:5:1:0 | 3.9 |
| 2 | 0:2:1:0 | 4.7 |
| 3 | 0:1:1:0 | 6.6 |
| 4 | 2:1:0:1 | 0.0 |
| 5 | 2:3:0:3 | 0.0 |
| 6 | 2:3:2:3 | 25.7 |
| 7 | 2:1:1:1 | 13.4 |

As can be seen, under anhydrous conditions the degree of succinylation was low and was somewhat improved by increasing the amount of pyridine. In the absence of pyridine (with $H_2O$ present), no succinylation occurred. In 20 percent $H_2O$, 20 percent pyridine, 25 percent succinylation was achieved. Increasing the amount of $H_2O$ decreased the overall yield. For optimum yield, the quantity of $H_2O$ appears to be 25 percent or less and the amount of pyridine appears to be 20 percent or higher.

Table 2, below, shows the relative mobilities and retention times for (3'-5') cyclic inosine monophosphate, succinylated (3'-5') cyclic inosine monophosphate and related compounds. The electrophoresis procedure (triethylammonium carbonate) separates the mononucleotides on the basis of charge at pH 7.5.

TABLE 2

| Compound | Chromatographic Properties | |
|---|---|---|
| | Mobility On Paper Electrophoresis (triethylammonium carbonate, 30 V/cm 45 min.) in mM | HPLC Retention Time, min. |
| (3'-5') cyclic inosine monophosphate | 69 | 9.8 |
| succinylated (3'-5') cyclic inosine monophosphate | 81 | 11.0 |
| Ethylenediamine treated succinylated (3'-5') cyclic inosine monophosphate | 69 | 9.8 |
| Inosine | 42 | 8.7 |
| 5'-inosine monophosphate | 94 | 2.9 |
| 5'-inosine diphosphate | 120 | 2.3 |

The relationships between mobility and charge are clearly shown in the increasing mobilities of inosine, inosine monophosphate and inosine diphosphate. The single negative charge carried by (3'-5') cyclic inosine monophosphate places it between inosine and inosine monophosphate. The succinylation reaction product migrates with almost the same mobility as inosine monophosphate on triethylammonium carbonate paper electrophoresis, but has a completely different retention time on HPLC. Because ester bonds are so sensitive to nucleophilic attack, (3'-5') cyclic inosine monophosphate was incubated with ethylenediamine (or ammonia) for one hour at 40° C. As can be seen from Table 2, the process converted the succinylated (3'-5') cyclic inosine monophosphate back to the starting material, (3'-5') cyclic inosine monophosphate. In a wide variety of storage and incubation conditions, succinylated (3'-5) cyclic inosine monophosphate was quite stable. Storage at 4° C. in 0.05M Tris-Cl, pH 7.6, for six months had no effect. This stability is in contrast to the extreme instability of 2'-O-succinyl inosine. Chemically synthesized 2'-O-succinyl inosine was stored in butanol at −20° C. After one week, 35 percent of the product had broken down to inosine. After three weeks, less than 10 percent of the 2'-O-succinyl inosine remained. The origin of this instability appears to be the presence of a free 3'-hydroxyl group in the chemically synthesized product. This in part may account for the difficulty in isolating 2'-O-succinyl inosine from succinylated 2'-O-polyinosinic acid.

The structure of the (3'-5') cyclic inosine succinate product was verified. It was observed that this product migrates with an additional negative charge compared to (3'-5') cyclic inosine monophosphate on paper electrophoresis (triethylammonium carbonate). When the (3'-5') cyclic inosine succinate and (3'-5') cyclic inosine monophosphate spots are cut out of the paper and eluted, both retain the correct Rf values on HPLC. Treatment of the (3'-5') cyclic inosine succinate with 2M ethylenediamine at 40° C. for one hour results in the destruction of the product. Following this treatment, only (3'-5') cyclic inosine monophosphate could be detected by electrophoresis and HPLC. Experiments with [$^{14}$C]-succinic anhydride (25 mCi/m Mol) revealed that [$^{14}$C]-(3'-5') cyclic inosine succinate comigrated with the nonradioactive (3'-5') cyclic inosine succinate on paper electrophoresis. Treatment of [$^{14}$C]-(3'-5') cyclic inosine succinate with 2M ethylenediamine resulted in separation of (3'-5') cyclic inosine monophosphate from the radioactive material by paper electrophoresis.

In another esterification procedure, the cetyl trimethylammonium salt of polyinosinic acid was reacted with succinic anhydride. The cetyl trimethylammonium salt was prepared by dissolving polyinosinic acid in water and adding excess cetyl trimethylammonium bromide dissolved in ethanol. The mixture was dialyzed against $H_2O$ to remove the ethanol and sodium bromide. As the dialysis proceeded, the cetyl trimethylammonium salt of polyinosinic acid precipitated. The resulting precipitate was collected by centrifugation and washed with $H_2O$. The washed precipitate was then dissolved in a 9:1 acetonitrile-$H_2O$ mixture. In order to insure replacement of the $Na^+$ counter ion the process was repeated. The resulting cetyl trimethylammonium salt of polyinosinic acid was then stored at 4° C. in $CH_3CN/H_2O$, 1:1.

Thereafter, the cetyltrimethyl ammonium salt of polyinosinic acid was diluted as indicated and succinic anhydride, dissolved in pyridine, was added thereto. After an appropriate period of time, the reaction was terminated by the addition of $H_2O$ and NaCl.

The resulting 2'-O-succinylated polyinosinic acid was purified by a series of ethanol precipitations in the presence of NaCl to insure complete replacement of the cetyl trimethylammonium cations by sodium cations. Excess succinic anhydride was also eliminated by this procedure. The extent of succinylation was determined by the incorporation of [$^{14}$C]-succinic acid into the 2'-O-succinylated polyinosinic acid.

The 2'-O-succinylated polyinosinic acid was degraded in a variety of ways in order to detect the 2'-O-succinyl inosine monomer. With the exception of phosphorolysis by PNPase and diphosphate removal by BAPase, all degradative procedures removed the succinyl group. For verification of 2'-O-succinyl inosine, a chemically synthesized standard was made.

2'-O-succinyl inosine was synthesized by using 1,3-dichloro-1,1,3,3-tetra isopropyldisiloxane as a block group for 3' and 5'-hydroxyl groups in accordance with known procedures. Starting material was separated from the (3'-5)-protected inosine by silica gel chromatography ($CHCl_3$:MeOH, 20:1). The protected nucleotide was dissolved in pyridine and excess succinic anhydride was added. The reaction was monitored by silica gel TLC ($CHCl_3$:MeOH, 20:1). Blocked, succinylated inosine was separated from starting material by silica gel column chromatography. The overall yield was 30 percent. The product was deblocked using tetraethylammonium fluoride to yield a single spot on TLC with an Rf of 0.46 on silica gel (40% $CHCl_3$:MeOH). Inosine has a mobility of 0.32. The product was stored in butanol at −20° C. [$^{14}$C]-succinylated polyinosinic acid (15–200 n Moles) was digested by PNPase (1 unit) in phosphorolysis buffer (10 mM $PO_4$, 0.5 mM $MgCl_2$, 50 mM Tris-Cl, pH 8.1) in accordance with known procedures. The reaction mixture was diluted with 30 mM Tris-Cl, pH 8.1 and BAPase (0.35 unit) was added. After one hour, the reaction mixture was spotted on silica gel TLC plates (40% $CHCl_3$:MeOH) with chemically synthesized 2'-O-succinyl inosine and inosine markers. UV-containing spots were cut out of the sample and marker lanes and counted. [$^{14}$C]-counts were found at the origin and comigrating with the chemically synthesized sample (both had Rf=0.46).

In the above esterification reactions a method was required to solubilize the polyinosinic acid in a mixed organic environment. As noted above, a known cetyl trimethylammonium salt procedure was utilized. The cetyl trimethylammonium salt of polyinosinic acid was not soluble in any pure organic solvent, nor in $H_2O$. However, this salt was soluble in a mixture of 10–20 percent water, the remainder being an organic solvent.

It was found that the succinylation of the cetyl trimethylammonium salt of polyinosinic acid yielded about 1–6 percent of the desired product. As observed in the succinylation of (3'–5') cyclic inosine monophosphates, increasing the quantity of pyridine in the presence of water greatly enhanced the overall succinylation.

Also, as noted above, the terminal free carboxyl group of the resulting ester, such as the succinates, described above, is amidated with a diaminoalkane, cysteamine or 2,2'-dithiobis(aminoethane) by conventional procedures.

A representative amide formation reaction is as follows. Amide bond formation was carried out at 0° C. by the addition of cysteamine (in 100 to 150 times excess the number of succinyl moieties) to a 2'-O-succinylated polyinosinic acid solution, defined above. The pH was then adjusted to 4.75 and a water soluble carbodimide, for instance, 1-ethyl-3-dimethyl-aminopropylcarbodimide was added with constant adjustment of the pH to 4.75. As the reaction progressed, the N-acylurea product precipitated as well as most of the reaction product of 2'-O-succinylated polyinosinic acid and cysteamine. The entire reaction was diluted tenfold with $H_2O$ and the precipitated material redissolved. The thus modified polyinosinic acid was purified from free amine by ethanol precipitation and Sephadex G-75 chromatography.

The extent of cysteamine incorporation was determined by conventional procedures employed for the determination of monothiols in macromolecules following reduction with dithiothreitol (DTT). This method can accurately detect monothiols at 0.2 percent substitution (1 in 500 nucleotides). Reduction of the reaction product of 2'-succinylated polyinosinic acid and cysteamine with DTT resulted in the presence of a monothiol group covalently attached to the polynucleotide. The monothiol comigrated with the polyinosinic acid on Sephadex G-75, and could be separated from the polynucleotide on Sephadex G-75 following treatment of the reaction product of 2'-O-succinylated polyinosinic acid and cysteamine with ethylene diamine. In addition, the reaction product of 2'-O-succinylated polyinosinic acid and cysteamine, reduced by DTT and repurified by Sephadex G-75, was retained on mercury agarose chromatography columns. The reaction product of 2'-O-succinylated polyinosinic acid and cysteamine was eluted specifically by beta-mercaptoethanol. Free polyinosinic acid or 2'-O-succinylated polyinosinic acid was not retained on mercury agarose columns.

The cysteamine addition to 2'-O-succinylated polyinosinic acid has been shown using a modified procedure of Hoare and Koshland, this procedure originally being quantitative for carboxyl groups in proteins. However, it was found that this procedure was not quantitative for the carboxyl groups in 2'-O-succinylated polyinosinic acid. Nonetheless by modifying the technique to use 0° C. rather than room temperature and by excluding urea from the reaction mixture, the technique was adapted for the present purposes. These modifications may well have contributed to the overall yield of 30 to 50 percent experienced.

The final product was examined for the percent cysteamine incorporation by conventional procedures and for the effect of the cysteamine addition process on the stability of the succinate moiety. By measurement of the amount of [$^{14}$C]-succinic acid attached to the 2'-O-succinylated polyinosinic acid and the reaction product of 2'-succinylated polyinosinic acid and cysteamine, no change in the amount of succinic acid was found. Treatment of 2'-O-succinylated polyinosinic acid and the reaction product of 2'-O-succinylated polyinosinic acid and cysteamine with ethylene diamine caused the release of all [$^{14}$C]-succinate and monothiol from the polyinosinic acid.

Care was taken to protect the monothiol group of the reaction product of 2'-O-succinylated polyinosinic acid and cysteamine. After purification, this monothiol group containing product was admixed with a Con A-SMPB, i.e., N-succinimidyl 4'-(p-maleimidophenyl) butyrate, product as disclosed below.

B. Bisulfite-catalyzed transamination of nucleic acids.

As indicated above, the C-4 amino group of cytosine can be replaced by diaminoalkanes via a transamination reaction.

Unlike proteins that contain several chemically reactive groups such as alkylamines, thiols, imidazoles and carboxyls, nucleic acids do not. In order to add macromolecules to nucleic acids, it is necessary to add thereto at least one of these functional groups.

It has been found appropriate, in the practice of the present invention to transaminate the cytidine residues in nucleic acids by alkyldiamine since the reaction is a simple and mild one, applicable to mononucleotides as well as polynucleotides. The resulting N-4-aminoalkyl group of the product can function as a reactive site for acylation with, for instance, N-hydroxy succinimide esters.

Representative transamination reactions are shown as follows:

Solutions of polyribocytidylic acid or polydeoxyribocytidylic acid were mixed in ten volumes of 2N $NaHSO_3$, 1M ethylene diamine, pH 7.0. The reaction mixture was incubated at 37° C. for an appropriate period of time. The reaction was terminated by the addition of three to four volumes of water, followed by dialysis against 30 mM Tes, 0.15M sodium chloride, pH 7.0. The polymers were precipitated with two volumes of ethanol. Aliquots were treated with RNase A or snake venom phosphodiesterase and alkaline phosphatase in Hepes, pH 7.5 and analyzed by HPLC.

The resulting modified polyribocytidylic acid possesses the identical UV absorption as polyribocytidylic acid. For quantitative analysis of the extent of reaction, the modified polymers, as noted above, were digested completely with RNase and bacterial alkaline phosphatase, and analyzed by HPLC. The presence of cytidine and aminoethylcytidine was confirmed by comparison to previously verified standards. Traces of uridine, indicating a small amount of deamination of cytidine was also detected. The modification rate of polyribocytidylic acid by ethylenediamine was significantly faster than that of methylamination and comparable to transamination of cytidine with propanediamine. All the cytidine residues were converted to aminoethylcytidine in four days. It has been found that an alkyldiamine of the formula $H_2N—(CH_2)_n—NH_2$ wherein n is 2–12 are useful in the present invention. As the alkylene chain becomes greater than ethylene, the rate of transamination appears to slow down, and the competing deamination reaction becomes more favorable. In the case of ethylenediamine, it has been found that only 4 percent of the cytidine residues were deaminated during a 39 hour reaction period, while, favorably, 61 percent were converted to aminoethylcytidine.

For the successful use of the aminoethyl cytidine modification as a site for subsequent chemical modification, such as conjugation to proteins and biotin, it has been found that 5 to 10% transamination is sufficient. This limited extent of modification can generally be achieved in a reaction period of about 2 to 4 hours. No uridine was detected by HPLC analysis.

Double-stranded complexes of a series of thus modified polyribocytidylic acid polynucleotides were examined for their thermal stability. Table 3, below, shows the Tm of this complex.

TABLE 3

Effect of transamination and biotinylation on Tm of $rI_n \cdot r(C_xAEC)_n$ and $rI_n \cdot r(C_xAECBio)_n$

| % substitution in polyribocytidylic strand | Tm $rI_n \cdot r(C_xAEC)_n$ [a] | $rI_n \cdot r(C_xAECBio)_n$ [b] |
|---|---|---|
| 0 | 66.0 | 62.7 |
| 4 | 65.3 | 60.3 |
| 9 | 65.0 | 59.3 |
| 19 | 57.2 | 54.5 |
| 32 | 46.7 | — |
| 49 | 34.7 | — |

[a] 0.15 M NaCl 0.01 M Hepes, pH 7.5
[b] 0.10 M NaCl 0.01 M Hepes, pH 7.5

From Table 3 it can be seen that the difference of Tm (melting temperature) between $rI_n \cdot rC_n$ and $polyI_n \cdot r(C_{10}AEC)_n$ is only 1.0° C. Thus, 9 percent transamination of the polyribocytidylic acid strand did not greatly affect the thermal stability of the complex. Like 4-methylcytidine, aminoethylcytidine residues appear to remain in the polyribocytidylic acid backbone, and participate in hydrogen-bonding with the hypoxanthine residues in poly(rI). A greater effect on Tm was found for $rI_n \cdot r(C_4AEC)_n$. The $r(C_4AEC)_n$ polymer was smaller in size (5.8 $S_{20,w}$ in 0.1×SSC) than the original polyribocytidylic acid (7.2 $S_{20,w}$ in 0.1 ×SSC). The melting curves of more extensively modified complexes were very broad. The effects of excessive modification on double-stranded complex formation indicate the total degree of substitution should be less than 10%.

Although transamination is a single-strand specific reaction, this modification procedure can also be applied to double-stranded DNA after heat denaturation. The initial transamination reactions with double-stranded DNA were performed using high temperature to prevent renaturation of DNA and to accelerate the reaction. The modified DNA was digested enzymatically and examined by HPLC for dAEC content. The dAEC produced had the same retention time on HPLC as the authentic material. The extent of reaction was exceedingly fast. Twenty percent of the cytidine residues was modified during a 10 minute incubation. The overall recovery of the DNA sample was 70-90 percent. These results suggest that precipitation of DNA in the presence of the high concentration of salt in the reaction did not occur during incubation. Agarose gel electrophoresis analysis of modified Hind III fragments of λ phage DNA (0.13-23.5 kb) showed a smear from about 3.5 kb to 0.1 kb. This analysis indicated that while the DNA chains were randomly nicked during the high temperature reaction, nonetheless the DNAs were not completely broken down to small molecules. Preferably then, a short incubation period, i.e. of up to about 5 minutes will yield a sufficient amount of aminoethylcytidine substitution.

When double-stranded DNA is treated with sodium bisulfite-ethylenediamine at 37° C. after boiling, the reaction rate of this transamination reaction is comparable to that of polyribocitydilic acid transamination reaction at 37° C. For a 5 hour reaction, 10 percent of the cytidine residues were modified. When the initial 100° C. treatment for 5 minutes is eliminated, it is observed that the reaction progresses extremely slowly. Since recovery of DNA in this reaction is about 70-90 percent, small fragments of DNAs do not precipitate during 37° C. incubation. It has been observed, however, that larger dsDNAs, such as calf thymus DNA, precipitated under these conditions.

In a specific experiment, DNA samples, prior to reaction, were denatured by boiling for five minutes. Immediately thereafter, nine volumes of 2N sodium bisulfite-1 methylene diaminohydrochloride at pH 7.5 were added and the reaction mixture was either maintained at 100° C. or incubated at 37° C. The reaction was terminated by the addition of three or four volumes of water. The resulting solutions were dialyzed against 0.5M NaCl, 10 mM Hepes, pH 7.5, and then against 0.1M NaCl, 10 mM Hepes, pH 7.5, and finally against 10 mM Hepes, pH 7.5. Final dialysis was performed at 37° C. for 8-15 hours to permit the pyrimidine-bisulfite adducts to convert back to the original base.

Aliquots were digested by DNase I in 0.1M Tes buffer, pH 6.5 at 37° C. for 8 to 15 hours, and then with snake venom phosphodiesterase and alkaline phosphatase at 37° C. for 12 to 15 hours. The digested samples were analyzed by HPLC.

C. Enzymatic modification of nucleic acids.

Enzymatic polymerization of aminoethylcylidine di- or tri-phosphate represents a milder method of obtaining modified polynucleotides, although it has been observed that substituted nucleotides do not effectively serve as subtrates. PNPase, DNA polymerase and terminal transferase were examined for the ability to use aminoethylcytidine modified di- or tri-phosphates as substrates.

Polynucleotide phosphorylase can polymerize ribonucleoside diphosphate in the absence of inorganic phosphate. Copolymerization of aminoethylcytidine diphosphate and cytidine diphosphate by PNPase is an alternative method to obtain $r(C_xAEC)_n$. It has been shown that aminoethylcytidine diphosphate is a good substrate for PNPase in the presence of cytidine diphosphate. When the input ratio of aminoethylcytidine diphosphate and cytidine diphosphate was 1:10 the resultant polymer has 7.3 percent aminoethylcytidine residues. Overall yield was 48 percent, which is comparable to the yield when cytidine diphosphate is polymerized alone. This polymer has 4-14 $S_{20,w}$ in 0.1×SSC.

As pointed out above, aminoethyldeoxycytidine 5'-triphosphate and aminoethylcytidine 5'-diphosphate can be prepared by sodium bisulfite catalyzed transamination of deoxycytidine 5'-triphosphate and cytidine 5'-diphosphate and ethylenediamine.

The synthesis of 4-aminoethylcytidine, 2'-deoxy-4-aminoethylcytidine, 4-aminoethylcytidine 5'-diphosphate and 2'-deoxy-4-aminoethylcytidine 5'-triphosphate was carried out using a modification of the Shulman et al process. 26.7 mg of cytidine (0.11 m mole) and 39 mg of cytidine 5'-diphosphate (9.086 m mole) were dissolved in 1 ml of 1.3N sodium bisulfite and 1M ethylenediamine hydrochloride, pH 7.0, and incubated at 37° C. overnight (15 to 20 hours). The reaction mixture was diluted 10-fold with 0.1M Tris-HCl buffer (pH 7.0) and incubated at 37° C. for 24 hours. 35 mg of 2'-deoxycytidine (0.14 m mole) and 32.4 mg of 2'-deoxycytidine 5'-triphosphate (0.055 m mole) were treated with 2N sodium bisulfite-1M ethylenediamine hydrochloride, pH 7.0, at 37° C. overnight and then diluted with 0.1M Hepes buffer, pH 7.5 and incubated at 37°C. for 24 hours. After the buffer treatment the pH of each reaction mixture was adjusted to 7 with HCl, and applied to an activated charcoal column. The column was eluted with a 50% ethanol-2% aqueous ammonia solution to elute the modified nucleosides and nucleotides.

The nucleoside derivative, 4-aminoethylcytidine was purified using a Dowex 50 column ($NH_4^+$ form). Elution of 4-aminoethylcytidine was carried out using a step gradient of 10 mM and then 1M ammonium acetate, pH 5.0. The yield was 59.4 percent (0.065 m Mol).

Isolation of aminoethylcytidine 5'-diphosphate was effected using a Dowex I column ($HCOO^-$ form) eluted with a linear gradient from 0 to 1M of formic acid. The formic acid was removed by evaporation at room temperature. Overall yield was 71.3 percent (0.06 m mole).

Because deoxycytidine was converted to deoxyaminoethylcytidine completely, no further purification was required. The final yield of deoxyaminoethylcytidine was 66.4 percent (0.092 m M).

The purification of 2'-deoxy.4-aminoethylcytidine-5'-triphosphate was achieved using a Sephadex A-25 column ($HCOO^-$ form), eluted with a 400 ml linear gradient (0.1 to 0.4M) of triethylammonium bicarbonate. Then the fractions of 2'-deoxy 4-aminoethylcytidine 5'-triphosphate were pooled and evaporated. Overall yield was 64 percent (0.035 m M).

As indicated earlier, the aminoethyldeoxycytidine 5'-triphosphate can be used as a substrate for DNA polymerase I to incorporate aminoethyldeoxycytidine residues into double-stranded DNA via a nick translation reaction.

The nick translation procedure using DNA polymerase I is widely employed to obtain labeled DNA probes. It has been shown that aminoethyldeoxycytidine triphosphate can function as a replacement of [$^{32}$p]dCTP. The incorporation of the $\alpha$-labeled [$^{32}$]-P-NTP plateaued after 200 minutes and 15 percent of the input labeled dTTP was incorporated. This corresponds to 10 percent of the cytidine residues replaced by aminoethyldeoxycytidine. The nick translation with aminoethyldeoxycytidine triphosphate was rather slow compared with deoxycytidine triphosphate as a substrate under identical conditions. The modification of the N-4 position of cytidine may make the aminoethylcytidine less favorable as a substrate for polymerase reaction. In accordance with this general procedure 65 $\mu$l of a reaction mixture containing 2 $\mu$g of Hind III fragments of $\lambda$ DNA, 1 m mole of aminoethyldeoxycytidine 5'-triphosphate, 1 m mole of dATP, dGTP, [$^3$H]dTTP (3 $\mu$Ci/ m mole), 5 mM $MgCl_2$ and 1 mM $\beta$-mercaptoethanol was treated with 2 $\mu$l of activated DNase I solution (0.14 $\mu$g/ml) for 2 minutes at room temperature. Then 4 $\mu$l of E. coli DNA polymerase I (5 $\mu$/ml) were added and the mixture incubated at 10° C. At the indicated times, aliquots were applied to PEI strips. These strips were eluted with a 1N HCl solution twice and the percent incorporation was determined.

Also, as indicated earlier, aminoethyldeoxy-cytidine 5'-triphosphate can be used as a substrate for deoxynucleotidyl terminal transferase.

This enzyme can catalyze the polymerization of deoxynucleoside triphosphates at the 3'-end of double-stranded DNA in the presence of $Co^{2+}$ ion. Hind III fragments of $\lambda$ DNA were employed as a primer, which contain a 3'-recessed end. The kinetics of incorporation of [$^{14}$C]dAECTP into acid insoluble material have been shown. After phenol extraction, the reaction mixture was chromatographed onto Sephadex G-50 column. This method showed that 2.3% of total radio-labeled triphosphate was found in the DNA fraction. This result indicates that mean chain length of deoxyaminoethylcytidine was 23 nucleotides. Therefore, a limited chain length of poly(dAEC) can be synthesized using this enzyme.

Also with this enzyme, coupled with chemical modification reactions, it is possible to obtain a partially modified poly(dC) tail at 3'-end double-stranded DNA. Single-stranded and double-stranded DNA have different reactivities for bisulfite-ethylenediamine mediating transamination at 37° C. Therefore, double-stranded DNAs which have single-stranded regions such as DNAs with poly(dC) tails can be modified predominantly at the single-strand portions. The partially modified poly(dC) tail can function as a cohesive end for molecular cloning, and also as a site of crosslinking for protein-nucleic acid conjugation. The PSV-II neoplasmid, cut with PVI I, was tailed with dCTP by conventional procedures. The chain length of this poly(dC) tail varied from 3 to 30 nucleotides. With a dC tail of less than 10, a modification time was selected to obtain 10 percent modification usually. This PSV-II neo-DNA with modified dC-tail was then reacted with biotinyl N-hydroxy succininide ester, as shown below, and assayed for binding activity on an avidin-agarose column. This product was retained on avidin-agarose and showed that DNA with a (dC) tail was transaminated and biotinylated. The biotinylated compound had the same migration as the starting material, PSV II neo DNA.

In this regard, the terminal transferase reaction was carried out under conventional procedures. 100 $\mu$l of the reaction mixture contained Hind fragments of $\lambda$ 10 $\mu$g, 5 m mole of [$^{14}$C] aminoethyldeoxycytidine 5',-triphosphate ($2 \times 10^5$ cpm), 172.5 units of terminal transferase (NEN form), 0.15M potassium cacodylate, pH 6.9, 1 mM $CoCl_2$, 0.1M Zn $(OAc)_2$ and 1.3 mM $\beta$-mercaptoethanol. The reaction mixture was incubated at 36° C. At the indicated times, aliquots were removed and analyzed by TCA precipitation. After 40 minutes, the reaction was terminated by incubation at 100° C. for 5 minutes and subjected to deproteinized phenol extraction. The aqueous layer was loaded onto a Sephadex G-50 column (0.9 $\times$ 14 cm). Void volume fractions were collected and the length of the aminoethyldeoxycytidine tails was determined. II—Linking Proteins to Nucleic Acids.

As indicated above, linkage of the protein to nucleic acids is accomplished initially by introducing an aminoethyl or thioethyl group into the nucleic acid as described in Section I, above. The amino or thio group is then employed as a reactive site for crosslinking with the protein. Various crosslinking agents can be employed and the following are a number of preferred procedures.

D. Reaction of nucleic acid aminoethyl group with a homobifunctional acylating agent.

A protein-nucleic acid conjugate was synthesized using, as a homobifunctional acylating agent, dithiobis(N-hydroxylsuccinimidyl propionic acid). This reagent has a N-hydroxysuccinimide group at both ends of the molecule, one of which reacts with the 2-amino group of the nucleic acid aminoethyl arm. The N-hydroxysuccinimide group at the other end of this acylating agent reacts with the amino groups of the protein.

The protein selected was ConA. Primary ConA has 12 lysine residues per monomer and the 3-dimensional structure of ConA has been determined. Commercially available purified ConA was further purified by conventional methods. This purification step eliminates all protease damaged ConA subunits which self-aggregate and precipitate with time. ConA thus re-purified was fourfold better than starting material in a mouse cell agglutination assay. Briefly ConA (1 mg/ml) was dissolved in 1.0% $NH_4HCO_3$ and incubated at 37° C. Overnight a precipitate forms that is removed by centrifugation. The supernatant is then dialyzed against $H_2O$ and finally Tes CM buffer (0.02M Tes, pH 7.5, 1.0 mM $CaCl_2$, 10 mM $MnCl_2$) and used fresh or frozen at −70° C.

Radioactive or cold $r(C_{20}AEC)_n$, 20 to 30 od, was dissolved in 1.0 ml of 10 mM concentration of Hepes, pH 7.8. A freshly prepared dimethylsulfoxide solution of dithio bis(N-hydroxylsuccinimidylpropionate) at a concentration of 2.9 mg/ml and 0.75 m was added to the $r(C_{20}AEC)_n$ solution. The reactions were incubated at room temperature for 15 minutes and the $r(C_{20}AEC)_n$ was quickly precipitated with ethanol. The precipitate was dissolved in 1 ml of 50 mM EPPS buffer, pH 8.5, and added to 22 to 25 mg of solid ConA fluorescein isothiocyanate, ConA(F), powder (3.5 to 4 mg protein) or to 10 mg ConA as described above. The reaction mixture was then incubated at 37° C. for 4 hours.

E. Reaction of nucleic acid aminoethyl group and protein with a heterobifunctional acylating agent.

A protein-nucleic acid conjugate was synthesized using, as a heterobifunctional acylating agent, N-succinimidyl (2-pyridyldithiopropionate).

The reaction of proteins with N-succinimidyl (2-pyridyldithiopropionate) introduces a reactive sulfhydryl group by the formation of an amide linkage of pyridyldithiopropionate with primary amino groups. This procedure is applicable to proteins with or without disulfide groups.

7 mg of ConA(F) in 2XPBS, 1 mM $CaCl_2$, 1M $MnCl_2$ and 0.1 M α-methyl mannoside were treated with 40 μl of 10 mM N-succinimidyl (2-pyridyldithiopropionate) in ethanol at room temperature for 20 minutes. The modified ConA was purified by Sephadex G-25 gel filtration, with 10 mM Tes, pH 6.5, as the buffer. The degree of substitution was 8 molecules of pyridyldisulfide per ConA tetramer and 61 percent of the substituted ConA maintained the ability to bind to Sephacryl 200 column in the absence of 2-methyl mannoside.

11 m Mole of radioactive $(C_{20}AEC)_n$ in 1 ml of 0.15M EPPS buffer, pH 8.5, was treated with 20 ml of 10 mM of N-succinimidyl (2-pyridyldithiopropionate) in ethanol at room temperature for 2 hours. The polynucleotide was repurified by Sephadex G-25 gel chromatography, then lyophilized. A final ratio of 5 molecules of pyridyldisulfide per polynucleotide chain was determined by the quantity of pyridine-2-thione released by dithiothreotol (DTT).

For conjugate formation, substituted $r(CAEC)_n$ was treated by 0.5 ml of 50 mM DTT for 1 hour and the product was purified by Sephadex G-50 in 10 mM Tes buffer, pH 6.5. Pyridyldisulfide ConA was added to the eluted $(CAEC)_n$ fraction immediately. The concentration of $(CAEC)_n$ and ConA was 0.56 μM and 11 μM, respectively. The coupling reaction was carried out at room temperature in the dark for 24 hours.

The resulting protein-nucleic acid conjugate was purified by two sequential affinity column chromatography procedures. Sephacryl 200 was employed to remove unreacted $(CAEC)_n$ and denatured ConA(F). 40 percent of the fluorescein was retained in the column, in the presence of 1 mM $CA^{++}$ and $Mn^{++}$, and in the absence of any sugar moieties. The retained compounds were eluted by 0.1M α-methyl mannoside containing buffer. 5 percent of radioactivity of $(CAEC)_n$ was found in this absorbed fraction. The second affinity column was poly(I) agarose which has an affinity for the polyribocytidylic acid portion of the hybrid molecule. The α-methyl mannoside eluted fraction was adjusted to 25% formamide and 1M NaCl, and loaded onto a STET agarose column. The unsubstituted ConA was washed off by elution with 0.1M α-methyl mannoside, 25% formamide, 1M NaCl and 50 mM Tes buffer, pH 6.5. Then the product was eluted with 0.1M α-methyl mannoside, 90% formamide and 10 mM Tes buffer, pH 6.5. 88 percent of radioactivity was eluted in this fraction. The eluted product was then dialyzed against 10 mM Tes buffer, pH 6.5.

The protein-nucleic acid conjugates synthesized with either dithiobis-(N-hyroxysuccinimidyl propionate) or N-succinimidyl(2-pyridyldithiopropionate) contain a disulfide bond that can be reduced, thereby permitting the separation of the nucleic acid and protein components. Cleavage was detected by Sephacryl 200 chromatography. The $r(CAEC)_n$ was found in the absorbed ConA(F) fraction. After treatment with 0.1M DTT, the radioactive $r(CAEC)_n$ was eluted in the absence of 0.1M α-methyl mannoside. This result indicates that the absorption of the radioactive $r(CAEC)_n$ to the Sephacryl 200 column resulted from the formation of a covalent, easily reduced disulfide linkage between $r(CAEC)_n$ and ConA(F).

F. Reaction of the protein amino groups with a heterobifunctional reagent and the reaction of the acylated protein with a modified nucleic acid.

A protein-nucleic acid conjugate was synthesized using, as a heterobifunctional acylating agent, N-succinimidyl 4-(p-maleimidophenyl) butyrate. The nucleic acid employed was polyinosinic acid and the protein was repurified ConA, as defined above.

The synthesis of the ConA-polyinosinic acid conjugate involves the following three steps. Initially, ConA is reacted with the heterobifunctional acylating agent, N-succinimidyl 4-(p-maleimidophenyl) butyrate. The resulting product is purified. Secondly, the cystaminyl moiety in $rI_nSCS$ is reduced by DTT and the polymer is purified. Thirdly, the resulting monothiol-containing polynucleotide was then mixed, in excess, with the N-succinimidyl 4-(p-maleimidophenyl) butyrate modified ConA. After incubation overnight at 4° C. the resulting protein-nucleic acid conjugate was purified by Sephacryl S-200 affinity chromatography.

More specifically, ConA in Tes CM buffer, pH 7.5, containing 20 mM dextrose (50–100 n Mol of ConA) was admixed with a large excess of N-succinimidyl 4-(p-maleimidophenyl) butyrate (8.0–15 mol). After a 30 minute incubation on ice, the thus modified ConA was separated from free N-succinimidyl 4-(p-maleimidophenyl) butyrate by gel permeation chromatography on Biogel P-6 using Tes Cm buffer. The void volume containing the modified ConA was then immediately used for synthesis of the conjugate, and a portion was exhaustively dialyzed against Tes CM buffer, pH 7.5, to remove any remaining glucose. The agglutination potential was then assessed.

In an early study when glucose was omitted from the reaction procedure, the N-succinimidyl 4-(p-maleimidophenyl) butyrate step destroyed the agglutination activity of the ConA. When the N-succinimidyl 4-(p-maleimidophenyl) butyrate reaction is carried out as described above, there is no effect on agglutination.

Simultaneously, $rI_nSCS$ was reduced by DTT under anaerobic conditions in 0.01M sodium acetate, 1 mM EDTA, pH 5.0. The actual amount of polynucleotide used depended on the extent of 2'-0-succinylcystaminyl substitution. For a reaction containing 60 nMol of ConA, sufficient $rI_nSCS$ was used to have 160 m Mol of monothiol present in the polynucleotide. After a 30 minute reduction period by DTT, the $rI_nSCSH$ was purified by Sephadex G-75 chromatography in 0.02M Tes buffer, pH 6.5.

After isolation from their respective columns, the (p-maleimidophenyl) butyrate modified ConA and the $rI_nSCSH$ were mixed together, the buffer adjusted to Tes CM, pH 6.5 and the reaction incubated overnight at 4° C.

The resulting protein-nucleic acid conjugate was purified by Sephacryl S-200 chromatography.

Prior to purification, polyribocytidylic acid, in molar excess, was added to the reaction mixture and the whole was then applied to the Sephacryl S-200 column and washed with Tes CM buffer, pH 6.5, until no more polyribocytidylic acid ran through. ConA containing fractions were eluted with Tes CM buffer, pH 6.5 plus 50 mM α-methyl mannoside. This product fraction was dialyzed against Tes CM buffer, pH 6.5. For storage, glycerol was added to 20 percent and frozen at −70° C.

Demonstration of ConA linkage to $rI_n \cdot rC_n$, complex of polyinosinic acid and polyribocytidylic acid, was shown by rechromatographing the α-methyl mannoside eluted peak on Sephacryl S-200. The ConA portion of the peak and the radioactivity, as [$^{14}C$]-succinic anhydride reacted with rIn again were eluted together by 50 mM α-methyl mannoside.

The ConA·$rI_n$ conjugate reaction is designed to be unidirectional. Because there are no free sulfhydryl groups in ConA to react with the maleimido portion of N-succinimidyl 4-(p-maleimidophenyl) butyrate, and no free amino groups in $rI_nSCSH$ to react with the succinimidyl side of N-succinimidyl 4-(p-maleimido-phenyl) butyrate, the chemical orientation of this heterobifunctional acylating agent in the conjugate is predetermined and there are no side products made during the crosslinking reaction. The only molecules present in the reaction mixture should be unused starting materials, $rI_nSCSH$ and ConA-(maleimidophenyl) butyrate, and the product.

The reaction was performed under conditions of monothiol moiety excess to ConA to attempt to drive the reaction toward maximum substitution of the ConA. In so doing, the need for two affinity chromatograph purification steps was eliminated, because all the modified ConA should theoretically contain at least one $rI_n$ molecule. As shown in Table 4, reaction 3, the average number of nucleotides per ConA tetramer is 300.

TABLE 4

Summary of ConA-$rI_n$ reactions

| | ConA Modification | | $rI_n$ Properties | | Final Product | |
|---|---|---|---|---|---|---|
| | | | | n | | n |
| | n Moles of | n Moles of | n Moles of free | Moles of Nucleo- | n Moles of | Moles of Nucleo- |
| Reaction | SMPB | ConA | SH | tide | ConA | tide |
| 1 | 23,400 | 150 | 33 | 2,060 | 20.1 | —* |
| 2 | 5,830 | 32 | 62 | 2,500 | 1.7 | —* |
| 3 | 9,600 | 60 | 160 | 26,000 | 11 | 3,300 |

*$rI_nSCSH$ employed was not radioactive.

Based upon the percent substitution of monothiol per inosine residue, this ratio represents two $rI_n$ polynucleotide chains per ConA tetramer. Based upon a Poisson distribution of two $rI_n$ chains per ConA tetramer, 13.5 percent of the ConA product purified by the aforementioned procedure was devoid of any $rI_n$ substitution.

FIG. 1 depicts the UV-monitor tracings for reactions 2 and 3 from Table 4. The figure shows the elution profile of the peak material. The overall recovery of ConA was from 5–19% of the input material in the peak (III). Approximately 10% of the ConA came out at the end of the column wash step (II). The remainder of the material, 70–85 percent, remained irreversibly bound to the affinity column. This low level of recovery was observed with untreated ConA preparations and was not the result of the reaction process.

G. Biotinylation of the ethylamino group of modified nucleic acid and of the amino groups of protein and the linking of the biotinylated nucleic acid to the biotinylated protein through an avidin bridge.

A protein-nucleic acid conjugate was synthesized by biotinylating the nucleic acid ethylamino group, biotinylating the protein amino groups and linking the thus biotinylated material together via an avidin bridge.

The affinity constant between glycoprotein avidin D and biotin is extremely high ($k\ dis = 1 \times 10^{-5}M$). Biotins covalently attached to macromolecules still maintain this high affinity for avidin. Therefore, bitoin-linked macromolecules can be bound to other biotin-linked molecules through an avidin bridge.

The introduction of biotin into proteins was effected by reacting biotinyl N-hydroxy succinimide with the free alkylamino groups in protein.

The nucleic acids which contain a newly introduced free alkylamino group by transamination, as discussed in Section I above, can also be biotinylated. Thus, the biotin-modified nucleic acids can be linked to the protein containing a biotin moiety by the avidin bridge technique.

The introduction of biotin into transaminated nucleic acids was carried out, preferably, in a 50% dimethylsulfoxide solution at pH 8.5 using a large excess of biotinyl N-hydroxylsuccinimide ester. The reaction mixture was analyzed by HPLC after complete enzymatic digestion. HPLC analysis of the enzymatic digestion of transaminated λDNA Hind III fragments and its biotinyl-N-hydroxysuccinimide reacted products shows that the peak of dAEC disappeared after the reaction, and a new peak with the identical retention time as an authentic sample of dAECBio was observed. The biotin-labeling reaction was quantitative under these conditions. It was also found that the same results were achieved in biotin-labeling of rCn, dCn and other double-stranded DNAs.

Another assay for the introduction of biotin into nucleic acids was the avidin-agarose chromatography analysis. Biotin containing molecules are retained in the column. Table 5, below shows the resuts of these assays.

TABLE 5

Percent retention of biotinylated nucleic acid on Avidin D Agarose Columns

| | |
|---|---|
| poly(CAEC)[a] | 13% |
| poly(C-AECBio)$_n$ | 94% |
| poly(C-AECBio)$_n$[b] | 85% |
| pSV2(dC)$_n$-Bio[b] | 96% |

[a]Column size, 2.7 ml; sample, 50 μg
[b]Column size, 0.5 ml; sample, 0.02 μg.
Room temperature As can be seen from the above data, biotinyl N-hydroxysuccinimide reacted transaminated nucleic acids were retained in this column, whereas non-biotin linked nucleic acids were eluted.

The biotinylation of each of aminoethyldeoxycytidine (219 od) and aminoethylcytidine (200 od) was carried out in 2 ml of 0.05M EPPS buffer, pH 8.5, by the addition of 13.6 mg of biotinyl N-hydroxysuccinimide ester (40μ mole) in 1 ml of dimethyl sulfoxide. The reactions were carried out at room temperature for aminoethyldeoxycytidine and 37° C. for aminoethylcytidine.

A second amount of biotinyl N-hydroxysuccinimide ester (6.8 mg) was added to the reaction mixture and incubation was continued for an additional 15 to 18 hours. The extent of reaction was monitored by HPLC. Starting material, biotinyl N-hydroxysuccinimide ester, was removed by DEAE Sephadex A-25 eluted with water. Overall yields were 92% for dAECBio (201.00 od) and 93% for rAECBio (185 od). Samples for NMR were prepared by paper chromatography and eluted using isopropanol:$H_2O$ (7:3 v/v).

The properties of the modified nucleosides and nucleotides are set forth in the following tables. Nucleosode di- or tri-phosphates were digested by alkaline phosphatase and analyzed by HPLC. Dephosphorylated products were shown to have retention times essentially the same as the corresponding nucleosides.

TABLE 6

NMR chemical shifts in $D_2O$

| | cytidine | | | | | | | |
|---|---|---|---|---|---|---|---|---|
| | H$_6$ | H$_5$ | H$_{1'}$ | H$_{2'}$ | | H$_{3'}$ | H$_{4'}$ | H$_{5'5''}$ |
| rC | 7.84 | 6.07 | 5.91 | 4.32 | | 4.21 | 4.15 | 3.92 3.82 |
| rAEC | 7.77 | 6.01 | 5.87 | 4.27 | | 4.16 | 4.09 | 3.78 3.74 |
| rAECBio | 7.76 | 6.00 | 5.91 | 4.30 | | 4.21 | 4.13 | 3.92 3.83 |
| dC | 8.10 | 6.26 | 6.23 | 2.51 | 2.39 | 4.46 | 4.10 | 3.86 3.73 |
| dAEC | 7.75 | 6.01 | 6.24 | 2.38 | 2.26 | 4.39 | 4.02 | 3.82 3.77 |
| dAECBio | 7.75 | 5.96 | 6.23 | 2.38 | 2.24 | 4.38 | 4.02 | 3.78 3.78 |

| | ethylenediamine | | | | | |
|---|---|---|---|---|---|---|
| | CH$_2$ | CH$_2$ | H$_2$ | H$_3$ | H$_4$ | H$_5$ | H$_g$ |
| rAEC | 3.67 | 3.20 | | | | | |
| rAECBio | 3.65 | 3.46 | | | | | |
| dAEC | 3.66 | 3.20 | 2.93 | 4.40 | 4.61 | 2.91 | 2.24 |
| dAECBio | 3.62 | 3.23 | 2.73 | 4.35 | 4.56 | 2.95 | 2.2 |
| | Biotin | | | | | | |

TABLE 7

Ultraviolet maxima and minima of nucleosides and nucleotides

| | pH | | max | | min |
|---|---|---|---|---|---|
| rC | $H_2O$ | 6.5 | 230(sh) | 270 | 249 |
| rU | | | 262 | | 230 |
| rAEC | | | 235 | 272 | 227 250 |
| rAECBio | | | 235 | 271 | 226 250 |
| rAECDP | $H_2O$ | | 235 | 273 | 225 250 |
| dC | | | | | |
| dU | | | | | |
| dAEC | $H_2O$ | | 235 | 271 | 227 249 |
| dAECBio | $H_2O$ | | 235 | 272 | 226 248 |
| dAECTP | | 7.5 (TEAB) | | 272 | 250 |

TABLE 8

Rf value of nucleosides on TLC (80% methanol-chloroform)-Silica gel

| | |
|---|---|
| rC | 0.44 |
| rU | 0.59 |
| rAEC | 0.02 |
| rAECBio | 0.39 |
| dC | 0.51 |
| dU | 0.58 |
| dAEC | 0.09 |
| dAECBio | 0.45 |

TABLE 9

Retention times of nucleosides on reversed phase HPLC (Partisil 00S-3)
The column was eluted with 0.2% acetonitrile for 20 minutes, 0.1 M ammonium acetate, pH 5.8, next on 0.2–5% linear gradient of acetonitrile in 0.1 M ammonium acetate, pH 5 for 5 minutes, then 5–50% linear gradient for 5 minutes in 0.1 M ammonium acetate buffer, pH 5.8. The flow rate was 2.5 ml/min.

| Nucleoside | Retention Time (min) | Nucleoside | Retention Time (min) |
|---|---|---|---|
| rC | 3.5 | dC | 6.0 |
| rU | 4.8 | dU | 8.6 |
| rAEC | 4.5 | dAEC | 8.1 |
| rAECBio | 24.9 | dAECBio | 24.8 |

The column was eluted with 0.2% acetonitrile for 20 minutes, 0.1M ammonium acetate, pH 5.8, next on 0.2–5% linear gradient of acetonitrile in 0.1M ammonium acetate, pH 5 for 5 minutes, then 5–50% linear gradient for 5 minutes in 0.1M ammonium acetate buffer, pH 5.8. The flow rate was 2.5 ml/min.

TABLE 10

Relative mobility value of nucleotides and nucleosides of on paper electrophoresis (a) in 0.05 M TEAB buffer (pH 7.5)
distance dC/distance from dC to dCTP

| dc | rAEC | CDP | rAECDP | dC | dAEC | dAECTP | dCTP |
|---|---|---|---|---|---|---|---|
| 0 | −0.14 | 1.0 | 0.70 | 0 | −0.11 | 0.76 | 1.0 |

(b) in 0.3 M morpholinium acetate, pH 3.5
distance from rC/distance from rC to rCMP

| rC | rU | rAEC | rCDP | rAECDP | rCMP |
|---|---|---|---|---|---|
| 0 | 0.57 | −0.57 | 1.57 | 1.29 | 1.0 |

H. Biological Activity of ConA-rI$_n$·C$_n$ conjugates

The ConA-rI$_n$·rC$_n$ conjugate and ethylenediamine-treated conjugate, discussed in Section F, were diluted in HBS+0.1% BSA. Two fold dilutions were made and 0.5 ml of each dilution were applied to trypsinized mouse L cells to assess agglutination, and cultures of HF 926 for measurement of induction of the antiviral state. Controls were ConA+rI$_n$·rC$_n$, ConA, ConA+rI$_n$·rC$_n$+α-methyl mannoside, and rI$_n$·rC$_n$. Agglutination was scored 1 hour and 6 hours after addition of the samples. Each dilution was scored as ++++ (cell aggregates of 500 or more), +++ (aggregates of 50 or more), ++ (aggregates of 25 or more), + (clump of 10 or more cells), ± (small clumps of 5 or fewer cells), and − (single cells). The minimum concentration for agglutination was the last dilution to cause agglutination. For most ConA samples there was a sharp endpoint.

For induction of the antiviral state in human fibroblasts, cultures were treated with the sample, diluted in 1×HBS plus 0.1% bovine serum albumin for one hour at 37° C., washed once with media, and all cultures were refed with DMEM+2% FCS. After 24 hours incubation all cultures were infected with VSV. When virus infection was complete in virus control cultures, the percent protection induced was determined.

As a control experiment, the effect of 2'-O-succinylation on dsRNA induction of interferon was examined. All preparations of rI$_n$S·rC$_n$ or rI$_n$SCS·rC$_n$ were equal in interferon inducing activity to rI$_n$·rC$_n$. All polymers tested were modified 5 percent or less. The 2'-O modification in general does not affect the base pairing or have a helix destabilizing like base-mispairing.

Referring, again to FIG. 1, the ConA-rI$_n$·rC$_n$ conjugates from both peak fractions and final washout fractions (II) were analyzed for biological activity by agglutination and induction of the antiviral state on HF926.

For agglutination, the controls included in Table 11, below as ConA, ConA+rI$_n$·rC$_n$, rI$_n$·rC$_n$, ethylenediamine treated ConA, and ethylenediamine treated rI$_n$·rC$_n$. All the ConA containing samples except ConA+ α-methyl mannoside, agglutinated mouse L cells to the same extent. Agglutination was measured by two fold dilution of each sample, so the statistical error in each sample is roughly 50 percent. Mixture of α-methyl mannoside with ConA decreases the agglutination approximately sixty fold.

TABLE 11

Assessment of ConA Agglutination

| Sample | Minimum Concentration for Agglutination (n Mole/ml) |
|---|---|
| (as seen in Table 4) | |
| Reaction 1 (peak) | 0.307 |
| Reaction 2-Fraction II | 0.343 |
| Reaction 2-Fraction III (peak) | 0.365 |
| Reaction 3-Fraction II | 0.635 |
| Reaction 3-Fraction III (peak) | 0.275 |
| Reaction 2-Fraction III | 0.300 |
| (Ethylene diamine treated) | |
| ConA | 0.327 |
| ConA-ethylenediamine treated | 0.327 |
| ConA + rI$_n$ · rC$_n$ | 0.327 |
| rI$_n$ · rC$_n$ (ethylenediamine treated) or rI$_n$ · rC$_n$ | — |

Figure 2:
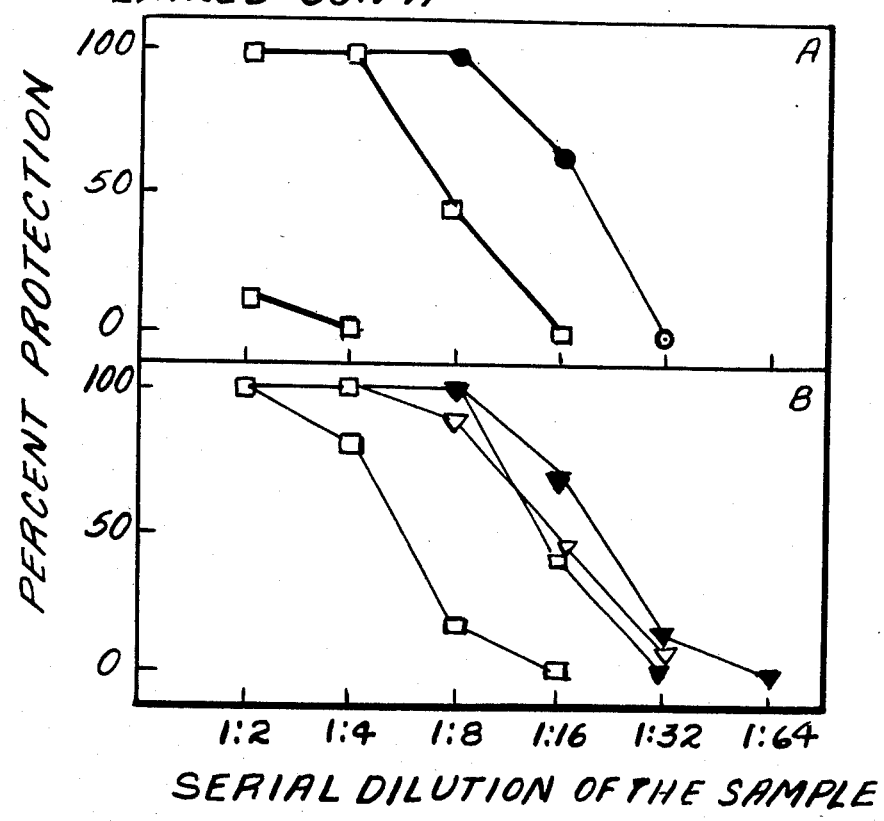

Referring now to FIG. 2, this shows the antiviral activity results obtained with the products from Reactions 2 and 3, shown in Table 4.

With regard to FIG. 2, the conjugate used in part A was from Reaction 2 of said Table 4. Dilutions of rI$_n$·rC$_n$-ConA conjugate □-□, ethylenediamine-treated rI$_n$·rC$_n$-ConA conjugate ●-●, and the rI$_n$·rC$_n$-ConA conjugate plus 30 mM α-methyl mannoside ■-■ were made in HBS+0.1% bovine serum albumin.

In part B of FIG. 2, dilutions of the rI$_n$·C$_n$-ConA conjugate, from Reaction 3 of said Table 4, were performed along with dilutions of ethylene diamine treated product □-□, free ConA plus rI$_n$·rC$_n$, and free rI$_n$·rC$_n$ ▼-▼. All samples were applied for 1 hour at 37° C. The samples were then removed and the cultures were washed 3 times and incubated overnight. All cultures were infected with VSV. One to two days later the cultures were stained with neutral red to determine the cytopathic effect.

As can be seen from FIG. 2, the product isolated from Reaction 1 can agglutinate mouse L-cells but had no antiviral activity. Fraction II from both Reactions 2 and 3 also lacked antiviral activity. As controls for the product for Reaction 2, ethylenediamine and α-methyl mannoside treated product samples were assessed in parallel. No free rI$_n$·rC$_n$ control was included.

Also, as shown in FIG. 2, α-methyl mannoside blocked some of the antiviral activity of the product. This effect was not as dramatic as the effect of α-methyl mannoside had on agglutination. Ethylenediamine had been shown previously to cleave the ester linkage in rI$_n$SCS and succinylated polyinosinic acid and not to alter the agglutination properties of ConA. Treatment of the ConA-rI$_n$·rC$_n$ complex with ethylenediamine resulted in an increase in antiviral effect compared to the intact molecule. The same result was found with the products of Reaction 3. Ethylenediamine treated product was a better inducer of the antiviral state than the ConA-rI$_n$·rC$_n$ complex. Because the ratio of ConA to rI$_n$SCSH was determined for the product from Reaction 3, controls of ConA plus rI$_n$·rC$_n$ and rI$_n$·rC$_n$ were included. ConA plus rI$_n$·rC$_n$ was equivalent in biological activity to ethylenediamine treated ConA-rI$_n$·rC$_n$ complex while free rI$_n$·rC$_n$ was slightly more effective.

The results shown in FIG. 2, parts A and B, indicate that the ConA-rI$_n$·rC$_n$ commmplex is biologically active and that the biological activity is disrupted by molecules which block the action of ConA. The fact that free rI$_n$·rC$_n$ in the presence of ConA is more active than the ConA-rI$_n$·rC$_n$ conjugate could be a result of the mechanism of rI$_n$·rC$_n$ activation of the antiviral state, and the known effects of ConA on interferon activity. The site of action of rI$_n$·rC$_n$ in human cells is the cell surface. If attachment of rI$_n$·rC$_n$ to ConA prevents interaction of rI$_n$·rC$_n$ with the rI$_n$·rC$_n$ receptor, then there would be a decrease in rI$_n$·rC$_n$-mediated activity. It has been shown that ConA can block the effects of interferon on cells in culture. This effect could be the reason for the slight difference in biological activity in rI$_n$·rC$_n$ and rI$_n$·rC$_n$ plus ConA.

Using avidin D there has been constructed a complex with a different carrier protein, i.e. beta-galactosidase using the technique set forth in Table 12, below.

TABLE 12

Use of Avidin: Biotin Interaction for Construction of rI$_n$ · rC$_n$-Carrier Protein Conjugate 1. Polyribocytidylic acid (rC$_n$) + ethylenediamine + sodium bisulfite→r(C$_{20}$ aminoethylcytidine)$_n$ [r(C$_{20}$AEC)$_n$]
2. r(C$_{20}$AEC)$_n$ + N—hydroxysuccinimide Biotin (Bio)→r(C$_{20}$AECBio)$_n$
3. rI$_n$ + r(C$_{20}$AECBio) + Avidin D→ rI$_n$ · r(C$_{20}$AECBio)$_n$:AVD
4. rI$_n$ · r(C$_{20}$AECBio)$_n$:AVD + bio.beta-glactosidase→

TABLE 12-continued
Use of Avidin: Biotin Interaction for
Construction of rI$_n$ · rC$_n$-Carrier Protein
Conjugate rI$_n$ · r(C$_{20}$AECBio)$_n$:avidin:bio-beta-glactosidase.

The biological activity of the complex is shown in FIG. 3.

Referring to FIG. 3, serial dilutions of rI$_n$·rC$_n$ plus Avidin ▭—▭ , rI$_n$·rC$_n$ avidin and bio-beta-glactosidase ○—○ , rI$_n$·rC$_n$ plus bio-beta-galactosidase △—△ , rI$_n$·rC$_n$ ▼—▼ , rI$_n$·C$_n$-bio , Avidin ●—● , rI$_n$·rC$_n$-bio Avidin bio-beta-galactosidase ▭—▭ and Avidin plus bio-beta-galactosidase ▼—▼ were performed in 1XHBS plus 0.1% BSA. All samples were applied to cultures of HF 926 for 1 hour at 37° C. The monolayers were washed 3 times with DMEM plus 2% FCS, refed and incubated overnight. All cultures were then infected with VSV and processed as before to determine the extent of induced antiviral state.

Unlike the results obtained with ConA, the rI$_n$·rC$_n$-Avidin-bio-beta-galactosidase complex was tenfold better than free rI$_n$·rC$_n$ at inducing the antiviral response in HF926. This procedure provides a method for the rapid screening of a variety of carrier proteins, because the biotination reaction is easy to perform. With this technique, the repetoire can be expanded to include cell-specific hormones and monoclonal antibodies.

From the studies described herein, several conclusions can be drawn. First, the method of linkage, through the rI$_n$ strand or the rC$_n$ strand does not appear to effect greatly the biological activity of the complexes. The major determinant of biological activity is the carrier protein.

In addition to inducing interferon and killing tumor cells, the procedure of the present invention is adaptable as a method for carrier protein directed delivery of DNA-specific gene therapy.

Also protein(s) possessing biological/bio-chemical activities (effector proteins) can be linked to nucleic acid in the aforementioned manner and can be brought inside the living cells together with the nucleic acid as a conjugate via the assistance of the carrier protein(s) which are also conjugated with the said nucleic acid. This conjugate can have higher biological activity exerted by either the biologically active proteins alone or the nucleic acid alone. Such an example is the function of interferon-rI$_n$·rC$_n$ conjugate system.

In summary, nucleic acid, such as rI$_n$·rC$_n$ can be conjugated with carrier protein(s) which direct the nucleic acid to a specific tissue or cell type. This same carrier protein or a second carrier protein can also promote/assist the uptake of the nucleic acid inside the living cell. In addition, the same nucleic acid can also be conjugated with other biologically active effector protein(s) along with the carrier protein(s). The nucleic acid-biochemically active protein(s)-carrier protein(s) conjugate can have a much greater biological activity due to synergism, when the conjugate is directed to and taken up by the targeted living cells in vitro and in vivo.

What is claimed is:

1. A method for producing a nucleic acid-protein conjugate which interacts with a living cell wherein the protein is specifically selected for the purpose of guiding the nucleic acid into said living cell, said method comprising
   (a) modifying said nucleic acid by esterifying the said nucleic acid with a saturated or unsaturated aliphatic dicarboxylic acid or an anhydride thereof and reacting the terminal free carboxyl group of the resulting ester with a diaminoalkane of the formula H$_2$N—(CH$_2$)$_n$—NH$_2$ wherein n is an integer from 2 to 12, so as to produce a modified nucleic acid containing a terminal amino group reactive with a bifunctional crosslinking agent and
   (b) reacting said bifunctional crosslinking agent with said modified nucleic acid and said protein.

2. The method of claim 1 wherein said bifunctional crosslinking agent is a homobifunctional acylating agent.

3. The method of claim 2 wherein said homobifunctional acylating agent is dithiobis (N-hydroxysuccinimidylpropionate).

4. The method of claim 1 wherein said bifunctional crosslinking agent is a heterobifunctional acylating agent.

5. The method of claim 4 wherein said heterobifunctional acylating agent is N-succinimidyl 2-pyridyldithiopropionate.

6. The method of claim 4 wherein said heterobifunctional acylating agent is N-succinimidyl-4'-(p-maleimidophenyl) butyrate.

7. The method of claim 1 wherein the amino group of said modified nucleic acid and the amino groups of said protein are reacted with a biotin-containing acylating agent and thereafter the biotin moieties of each are reacted with glycoprotein avidin or vitamin H avidin.

8. The method of claim 7 wherein the biotin-containing acylating agent is biotinyl N-hydroxysuccinimide.

9. The method of claim 1 wherein the amino group of said modified nucleic acid and the amino groups of said protein are reacted with a biotin-containing acylating agent and thereafter the biotin moieties of each are reacted with a monoclonal antibody.

10. A method for producing a nucleic acid-protein conjugate which interacts with a living cell wherein the protein is specifically selected for the purpose of guiding the nucleic acid into said living cell, said method comprising
    (a) modifying said nucleic acid by esterifying said nucleic acid with a saturated or unsaturated aliphatic dicarboxylic acid or an anhydride thereof and reacting the terminal free carboxyl group of the resulting ester with cysteamine so as to produce a modified nucleic acid containing a terminal thio group reactive with a bifunctional crosslinking agent, and
    (b) reacting said bifunctional crosslinking agent with said modified nucleic acid and said protein.

11. The method of claim 10 wherein said bifunctional crosslinking agent is a homobifunctional acylating agent.

12. The method of claim 11 wherein said homobifunctional acylating agent is dithiobis(N-hydroxysuccinimidylpropionate).

13. The method of claim 10 wherein said bifunctional crosslinking agent is a heterobifunctional acylating agent.

14. The method of claim 13 wherein said heterobifunctional acylating agent is N-succinimidyl 2-pyridyldithiopropionate.

15. The method of claim 13 wherein said heterobifunctional acylating agent is N-succinimidyl-4'-(p-maleimidophenyl) butyrate.

16. The method of claim 10 wherein the protein is acylated with, as a heterobifunctional reagent, N-succinimidyl-4'-(p-maleimidophenyl) butyrate and the terminal thio group of said modified nucleic acid reacts with the maleimido moiety of said acylated protein.

17. A method for producing a nucleic acid-protein conjugate which interacts with a living cell wherein the protein is specifically selected for the purpose of guiding the nucleic acid into said living cell, said method comprising
   (a) modifying said nucleic acid by esterifying said nucleic acid with a saturated or unsaturated aliphatic dicarboxylic acid or an anhydride thereof and reacting the terminal free carboxyl group of the resulting ester with 2,2'-dithiobis (aminoethane) so as to produce a modified nucleic acid having a terminal disulfide group adaptable to be reactive with a bifunctional crosslinking agent, and
   (b) reacting said bifunctional crosslinking agent with said modified nucleic acid and said protein.

18. The method of claim 17 wherein said bifunctional crosslinking agent is a homobifunctional acylating agent.

19. The method of claim 18 wherein said homobifunctional acylating agent is dithiobis (N-hydroxysuccinimidylpropionate).

20. The method of claim 17 wherein said bifunctional crosslinking agent is a heterobifunctional acylating agent.

21. The method of claim 20 wherein said heterobifunctional acylating agent is N-succinimidyl 2-pyridyldithiopropionate.

22. The method of claim 20 wherein said heterobifunctional acylating agent is N-succinimidyl-4'-(p-maleimidophenyl) butyrate.

23. A method for producing a nucleic acid-protein conjugate which interacts with a living cell wherein the protein is specifically selected for the purpose of guiding the nucleic acid into said living cell, said nucleic acid containing cytosine, said method comprising
   (a) modifying said cytosine containing nucleic acid by transaminating said nucleic acid by reacting it with a diaminoalkane in the presence of an alkali metal bisulfite whereby the bisulfite forms an adduct with said cytosine and whereby the diaminoalkane displaces the C 4-amino group so as to produce a modified nucleic acid having a terminal aminoalkyl group reactive with a bifunctional crosslinking agent, and
   (b) reacting said bifunctional crosslinking agent with said modified nucleic acid and said protein.

24. The method of claim 23 wherein said bifunctional crosslinking agent is a homobifunctional acylating agent.

25. The method of claim 24 wherein said homobifunctional acylating agent is dithiobis (N-hydroxysuccinimidylpropionate).

26. The method of claim 23 wherein said bifunctional crosslinking agent is a heterobifunctional acylating agent.

27. The method of claim 26 wherein said heterobifunctional acylating agent is N-succinimidyl 2-pyridyldithiopropionate.

28. The method of claim 26 wherein said heterobifunctional acylating agent is N-succinimidyl-4'-(p-maleimidophenyl) butyrate.

29. A method for producing a nucleic acid-protein conjugate which interacts with a living cell wherein the protein is specifically selected for the purpose of guiding the nucleic acid into said living cell, said nucleic acid containing cytosine, said method comprising
   (a) modifying said cytosine containing nucleic acid by transaminating said nucleic acid by reacting it with cysteamine in the presence of an alkali metal bisulfite whereby the bisulfite forms an adduct with said cytosine and whereby the amino group of the cysteamine displaces the C 4-amino group so as to produce a modified nucleic acid having a terminal thiol group reactive with a bifunctional crosslinking agent, and
   (b) reacting said bifunctional crosslinking agent with said modified nucleic acid and said protein.

30. The method of claim 29 wherein said bifunctional crosslinking agent is a homobifunctional acylating agent.

31. The method of claim 30 wherein said homobifunctional acylating agent is dithiobis (N-hydroxysuccinimidylpropionate).

32. The method of claim 29 wherein said bifunctional crosslinking agent is a heterobifunctional acylating agent.

33. The method of claim 32 wherein said heterobifunctional acylating agent is N-succinimidyl 2-pyridyldithiopropionate.

34. The method of claim 32 wherein said heterobifunctional acylating agent is N-succinimidyl-4'-(p-maleimidophenyl) butyrate.

35. A method for producing a nucleic acid-protein conjugate which interacts with a living cell wherein the protein is specifically selected for the purpose of guiding the nucleic acid into said living cell, said nucleic acid containing cytosine, said method comprising
   (a) modifying said cytosine containing nucleic acid by transaminating said nucleic acid by reacting it with 2,2'-dithiobis(aminoethane) in the presence of an alkali metal bisulfite whereby the bisulfite forms an adduct with said cytosine and whereby the amino group of said 2,2'-dithiobis (aminoethane) displaces the C 4-amino group so as to produce a modified nucleic acid having a terminal disulfide group adaptable to be reactive with a bifunctional crosslinking agent, and
   (b) reacting said bifunctional crosslinking agent with said modified nucleic acid and said protein.

36. The method of claim 35 wherein said bifunctional crosslinking agent is a homobifunctional acylating agent.

37. The method of claim 36 wherein said homobifunctional acylating agent is dithiobis (N-hydroxysuccinimidylpropionate).

38. The method of claim 35 wherein said bifunctional crosslinking agent is a heterobifunctional acylating agent.

39. The method of claim 38 wherein said heterobifunctional acylating agent is N-succinimidyl 2-pyridyldithiopropionate.

40. The method of claim 38 wherein said heterobifunctional acylating agent is N-succinimidyl-4'-(p-maleimidophenyl) butyrate.

41. A method for producing a nucleic acid-protein conjugate which interacts with a living cell wherein the protein is specifically selected for the purpose of guiding the nucleic acid into said living cell, said method comprising (a) modifying said nucleic acid enzymatically to incorporate aminoethyldeoxycytidine or aminoethylcytidine residues therein and
(b) reacting a bifunctional crosslinking agent with said modified nucleic acid and said protein.

42. The method of claim 41 wherein said bifunctional crosslinking agent is a homobifunctional acylating agent.

43. The method of claim 42 wherein said homobifunctional acylating agent is dithiobis(N-hydroxysuccinimidylpropionate).

44. The method of claim 41 wherein said bifunctional crosslinking agent is a heterobifunctional acylating agent.

45. The method of claim 44 wherein said heterobifunctional acylating agent is N-succinimidyl 2-pyridyldithiopropionate.

46. The method of claim 44 wherein said heterobifunctional acylating agent is N-succinimidyl-4'-(p-maleimidophenyl) butyrate.

47. A nucleic acid-protein conjugate made in accordance with any one of claims 1–46.

* * * * *